United States Patent [19]

Heinicke

[11] Patent Number: 4,543,212

[45] Date of Patent: * Sep. 24, 1985

[54] XERONINE, A NEW ALKALOID, USEFUL IN MEDICAL, FOOD AND INDUSTRIAL FIELDS

[75] Inventor: Ralph M. Heinicke, Honolulu, Hi.

[73] Assignee: Research Corporation of the University of Hawaii, Honolulu, Hi.

[ * ] Notice: The portion of the term of this patent subsequent to Oct. 11, 2000 has been disclaimed.

[21] Appl. No.: 530,689

[22] Filed: Sep. 9, 1983

Related U.S. Application Data

[60] Division of Ser. No. 329,953, Dec. 11, 1981, Pat. No. 4,409,144, which is a continuation-in-part of Ser. No. 870,919, Jan. 19, 1978, abandoned.

[51] Int. Cl.[4] .................. C07G 17/00; C07C 103/52; A01N 63/02; C12N 9/48; C12N 9/50

[52] U.S. Cl. ................. 546/1; 260/112.5 R; 424/94; 435/212; 435/219; 424/195.1; 514/810; 426/34; 426/18

[58] Field of Search ..................... 260/112.5 R, 236.5; 424/94; 435/212, 219

[56] References Cited

U.S. PATENT DOCUMENTS 4,409,144 10/1983 Heinicke ..................... 260/112.5 R Primary Examiner—Delbert R. Phillips
Attorney, Agent, or Firm—James C. Wray

[57] ABSTRACT

Described herein are the composition, the characterization, the assay, the mode of action and the utility of a new alkaloid which may be isolated from a wide variety of natural materials by observing certain techniques and precautions herein set forth.

5 Claims, No Drawings

XERONINE, A NEW ALKALOID, USEFUL IN MEDICAL, FOOD AND INDUSTRIAL FIELDS

BACKGROUND

This application is a division of application Ser. No. 329,953, filed 12/11/81, now U.S. Pat. No. 4,409,144 issued 10/11/83, which is a CIP of Ser. No. 870,919 filed 1/19/78, abandoned.

Certain natural products, such as various enzymes, herbs, and plant extractives are used in medicine, food technology, and industry to perform critical functions. For example a range of "crude enzyme" products are used as the basis for preparing oral antiinflammatory drugs. Bromelain, papain, amylase, pancreatin, chymotrypsin, a protease from *Serratia marcescens* and egg white lysozyme are all occasionally effective as oral antiinflammatory agents. Unfortunately even though all of these enzymes may be rigidly standardized for the named enzyme, the pharmacological effectiveness of different batches of these enzymes varies greatly. Obviously all of the members of this wide range of enzymes contain some pharmacologically active ingredient other than the named enzyme. If the nature and composition of this unknown ingredient could be identified and standardized, then preparations could be made which would be more effective than the improperly standardized present products and new applications could be developed, since the new product would be reliable. This is one of the objectives of the present invention.

In food technology three of the most important applications of "enzymes" are the "chillproofing" of beer, the in vivo and in vitro tenderization of meat, and the preparation of "instant" cooking cereals. Although proteases are used in all of these applications, in no case is there any correlation between proteolytical activity and effectiveness of the preparation. Swift & Co. after much research on their "proten" process found that no known enzyme test could distinguish between effective and non-effective batches of enzymes. On the whole they found that the most proteolytically active samples of papain were the least effective meat tenderizing agents. Since each assay on living animals cost them (1963 figures) $25,000, the importance of this problem can readily be appreciated. The Cream of Wheat Co. in a patented process attempted to use proteases to prepare "instant cooking" cereal. They had so much difficulty in getting reproducible results even though they purchased enzymes having exactly the same specifications from the same company, that for many years they discontinued using the process. Formulators of beer "chillproofing" preparations have long realized that each new batch of enzyme which they bought was a gamble. They have never been able to formulate their products on the basis of "proteolytic activity." Instead the better fomulators all rely solely upon laboratory use-tests in which the batches of enzymes are evaluated on the basis of their "chill-proofing" ability. If a simple, meaningful assay could be devised which would give a proper evaluation of performance, their costs would be greatly reduced. There have also been some interesting potential application of "enzymes" which have never developed commercially since one batch of "enzyme" might perform satisfactorily whereas the next batch from the same company and having precisely the same specifications would be worthless. The production of better flavored cocoa and vanilla are two examples of such applications.

Three things convinced me that the primary active ingredient in all these "enzymes" was something other than an enzyme; (1) the enzyme rationale for pharmacological activity was completely incompatible with accepted physiological and anatomical data, (2) both clinical and laboratory data showed a lack of correlation between enzymatic activity, and pharmacological action, and (3) certain (but not all) boiled enzyme preparations were as active as were the unheated enzyme preparations. Although certain clues quickly suggested to me that the active ingredient was a small molecule rather than a protein or large polypeptide, working out the details by which this small molecule is produced to be a difficult problem. The final solution of this problem now makes it possible to both describe useful methods for producing products containing the active ingredient and to suggest many new combinations and applications for the future.

RELATIONSHIP OF THE PRESENT INVENTION TO PREVIOUS KNOWLEDGE AND PRACTICES

The present invention differs from all previous practices and knowledge of the use of oral antiinflammatory enzyme as well as certain branches of folklore medicine which also treat inflammation, high blood pressure, and many other ailments in that this invention identifies the active ingredient, describes how the active ingredient is produced in the plant or animal, gives directions for liberating and isolating the active ingredient or its precursor, develops a theory of how the active ingredient works in pharmacological, physiological, food and industrial applications, and suggests and illustrates new applications for the active ingredient.

By contrast in the herbal folklore field, either no attempt is made to identify the active ingredient or else the active ingredient is incorrectly identified. Thus although many investigators have investigated the active ingredient in genseng, the very fact that every other year additional materials are isolated and claimed to be the active ingredient shows that the true nature of the active ingredient continues to elude the investigators. Perhaps the most eggregious example of a misidentification of an active ingredient occurs with "Laetrile," a reputed cure for cancer. The unfortunate designation of amygdalin as the active ingredient of "Laetrile" has caused the waste of million of dollars both on research and on futile use of the material. A few investigators have correctly pointed out that perhaps the wrong material was being isolated from almonds. However, these investigators have been unable to identify the nature of the active ingredient which is occasionally accidentally in the product.

Another classical example of the misidentification of the active ingredient in a potentially valuable product is the reputed identification of proteases as the pharmacologically active ingredient in bromelain, pancreatin, chymotrypsin, and *Serratia marcescens* protease. Thus, since these products are incorrectly standardized to contain identical amounts of protease activity, the biological activity varies greatly between different batches of product. For example Dr. Klein found that different batches of bromelain varied greatly in their ability to remove burn eschars, (incidentally this is one of the few medical applications of a protease which theoretically appears to be justified. However, cooperative work which Dr. Klein and I did showed that the protease activity was unrelated to the debridement of burn eschars.) Dr. G. Gerard of France showed that different batches of bromelain varied in their ability to cure certain types of cancer. Thus this potentially valuable remedy could never be recommmended as a cure.

The only published work which makes a new suggestion for a specific ingredient for bromelain is that of Klein and Houck, U.S. Pat. No. 4,197,291. Klein and Houck isolated and described a non-proteolytic hydrolytic enzyme which they believe is the active ingredient of bromelain. However, these authors were neither able to identify the nature of the substrate for this enzyme nor could they describe what the enzyme did at the molecular level. Although these authors call their enzyme a hydrolytic enzyme, the only evidence which they cite is the clinical evidence that the enzyme promotes the debridement of burn eschars by a collagenase type action. Their data on the size of the enzyme and its dimer or trimer nature are excellent.

The enzyme which these authors have isolated appears to be identical to the one which I had shown was necessary for the liberation of the active ingredient in 1972. Since I was searching for the ultimate molecule which was responsible for pharmacological activity, I merely considered the enzyme as one part of several components which were necessary to finally liberate the active substance. Without a proper substrate, the enzyme is worthless. My personal belief, which is based upon my discovering that xeronine is biologically active down to concentrations of $10^{-10}$ g/g of tissue, is that the enzyme which they isolated was contaminated by xeronine and that the adsorbed zeronine, not the enzyme, was responsible for the biological activity which they observed. Thus their product would—similar to bromelain—be standardized on the basis of the incorrect ingredient.

A similar situation occurs with chymotrypsin, a widely used oral antiinflammatory agent. Since chymotrypsin is isolated from the pancreas and since I had previously found that certain batches of pancreatin contained xeronine, I felt that trace amounts of xeronine might have been adsorbed on the protein during the isolation procedures. After heating a solution of chymotrypsin to 85 C. for five minutes, I found that the solution contained no protease activity but still contained 3 CAU of zeronine activity per mg, a figure similar to that of many bromelain samples.

From these examples—and many more could be cited—it is readily apparent that in the areas mentioned, the present practices and knowledge are inadequate to solve the problems for which the products are being recommended. My invention will greatly advance the treatment of certain medical problems, the modification of certain food products, and the recovery of certain industrial waste products by providing preparations which are standardized to contain the active ingredient for these various applications.

DETAILED DESCRIPTION OF THE INVENTION

XERONINE, Chemistry

Alkaloid Nature: The alkaloid nature of xeronine is attested to by the method used for isolation and purification of the material, by its changes in the UV spectrum when it is heated, by its behaviour in a mass spectrum analysis instrument and by its chemical reactions. In addition its odor is very similar to other alkaloid materials and is sufficiently distinctive so that once a person has been exposed to the odor, he can readily recognize the odor in other preparations.

During the isolation and purification procedures, the active ingredient behaves as a classical base. At pH values above 7.8 it can readily be extracted from aqueous solutions into such organic solvents as chloroform, ethylacetate, ether, or butanol. By extracting the organic layer with weak acid solutions, the alkaloid can be taken up in the aqueous phase.

This phase transfer procedure should be repeated several times. During the initial extraction into the organic solvent layer, the base is accompanied by steroids and camphor. Apparently xeronine can associate quite firmly with these lipids with the result that in the first extraction of the base from the organic layer, some of the xeronine remains in the organic layer with the lipids and some of the neutral lipds are extracted into the acidic water phase with the zeronine. However, after several reextractions the separation is clean.

Although the isolation procedures prove that the active ingredient is a base, it does not provide any clues regarding the nature of the base. When the active ingredient is isolated by gentle techniques, that is without exposure to high or low pH values or heat, it contains no free amino groups as measured by the ninhydrin reaction. However, if the material is heated strongly on a chromatographic plate, it finally reacts with ninhydrin to give an organish pink color which is not typical of a free amine. If, on the other hand, the active ingredient is heated with acid or base, then the material gives a typical ninhydrin color. These reactions prove that the nitrogen is originally present either in a secondary or tertiary form.

The changes which occur when the active ingredient is heated under different pH conditions give the most valuable information about the nature of the molecule. If the material is heated at about 60 C. for about 24-48 hours, the original essentially flat UV spectrum develops a very sharp and intense peak at 280 nm. On the other hand if a solution of the active ingredient is heated at pH 9.5 at about 80-90 C. for ten minutes a very strong peak develops at 253 nm. If the pH of either the original solution, or the 280 nm solution, or the 253 nm solution is adjusted to pH 12 and the solution is warmed slightly a new sharp peak appears at 245 nm and the 253 and the 280 nm peaks disappear completely.

The lack of any UV absorption except at low wavelengths indicates a molecule which contains no double bonds or other UV chromophores. The formation of forms of xeronine which absorb strongly at 280, 253 or 245 nm suggest dehydration of hydroxyl groups attached to non-aromatic rings with the formation of double bonds. The interconversion of three forms of the molecule into a fourth form, namely the one absorbing at 245 nm indicates that the molecule must have several OH groups on several different non-aromatic rings. At different pH values dehydration occurs at different parts of the rings. Apparently the 245 nm is the most stable form since it cannot be reconverted to the other forms. The 245 nm form has no biological activity but is valuable as a potential assay tool.

Although all attempts to obtain useful mass spectral on the active substance have been unsuccessful so far, even the lack of definitive data supports the picture of a fairly complex alkaloid. Since the alkaloid is volatile enough to give a definite odor in the free base form, one would expect that there would be no problem in getting a definitive mass spectrum analysis of the product. Yet all of the tests which have been run so far indicate that the molecule is so labile, that when it is bombarded by electrons, to form the molecular ion, the molecule fragments into a wide range of break down products. With one particularly good sample which was obtained by distilling the alkaloid from a basic aqueous solution at pH 9, and then picking up with a needle the crystals which float on the surface of the liquid at 30 and 50 C. two small peaks were obtained which had a mass of 414 and 428. At higher temperatures these peaks were part of a complex spectrum of products which continued to a mass of 518. Further data are required to get a definitive mass for the molecule. However, temporarily I am assuming that the molecular weight is 428, that the 414 peak represents the loss of nitrogen (although this is difficult to explain) and that the heavier mass peaks at higher temperatures represent aggregations of fragments of the molecule. As a minimum at this stage of the study we can feel confident that the molecular weight must be between 413 and 518. However, since the material has a definite odor at room temperature, I believe that the 428 mass may be the correct one.

The data from gel filtration would be completely compatible with a molecular weight of 428. When preparations of the active factor grossly contaminated with salts, sugars, peptides and amino acids are run on a gel filtration column (Sephadex G-15), the biological activity appears after the simple salts and sugars. This indicates a molecule which is small enough to enter the pores of the gel but is large enough so that when it diffuses out the pores it diffuses out after the simple sugars and amino acids. The UV spectrum of this fraction shows that it contains a mixture of presumably the 253 nm form of the active substance and peptides. The peptides were identified by the ninhydrin reaction.

ASSAY OF XERONINE

Spectrographic Method: This method is based on the irreversible conversion of the biologically active forms of xeronine to a form absorbing strongly at 245 nm by warming a solution containing xeronine at pH 12, dropping the pH between 3 and 7 and then comparing the spectral difference between a treated and an untreated sample.

The results are expressed as 245 nm Difference Units (DU) per unit of sample.

The method is very sensitive and specific for relatively pure preparations of xeronine. However, when it is used on crude enzyme solutions a variety of other materials also undergo a structural shift which is not reversible by re-adjusting the pH. Some of these materials absorb close enough to 245 nm to affect the height of the peak. Nevertheless even with crude enzyme preparations the method has good comparative value between different batches of enzymes.

Casein Aggregation Method (CAU)

For routine laboratory work this is the most convenient method since it is rapid, many samples can be handled at the same time, it is inexpensive, and it is sensitive. This assay is based on my discovery that xeronine can simulate certain of the reactions of rennet; xeronine can liberate a peptide from casein which leads to aggregation of the casein.

This method does have certain shortcomings. However, if the limitations are recognized and handled, the method is reliable.

The principal interfacing materials are proteases, excessive salt concentration, certain divalent cations (especially calcium), and excessive amounts of cysteine. The protease problem can be easily handled by placing the sample carefully in the bottom of a test tube and then heating the entire test tube in a boiling water bath for 5 minutes. The salt problem can generally be handled by dilution. Ammonium acetate, the salt which will be most commonly encountered in xeronine samples prepared by adsorption on weak cation columns, will interfere in the assay at concentrations down to $\frac{1}{4}$ saturated solutions. Below this level they rarely cause a problem. Cysteine is occasionally a problem since it must be added to certain steps in the preparation of xeronine to keep the precursor from forming disulfides. Adding a relatively insoluble mercury salt in excess, such as ethyl mercuric chloride, does not interfere in the reaction and quickly eliminates the excess cysteine.

The casein aggregation test may detect and assay both free xeronine and occasionally proxeronine. Free xeronine reacts immediately with casein to form an aggregation as soon as the solution is heated to 45 to 55 C. Proxeronine does not cause a reaction. However, certain batches of casein have as a contaminant an enzyme which, if other factors are present, can liberate zeronine from proxeronine. Heating the casein solution to 85–90 C. destroys this enzyme. If this enzyme is present in casein and if the sample contains proxeronine plus accessory factors, then the casein solution gradually becomes turbid over a period of an hour. This is definitely an enzyme reaction which can be readily recognized and distinguished from the rapid aggregation of casein caused by free xeronine.

In most of my studies I have purposefully prepared a crude casein solution from unpasteurized milk. This contains a maximum amount of both the enzyme (proxeroninase) as well as part of the accessory factors required for the enzymatic liberation of xeronine from proxeronine. Rather than using casein solutions which are designed to give a classical clotting of the casein, I also purposefully use less calcium than is normally recommended for casein aggregation reactions. This gives a solution which is generally clear enough to read in a spectrophotometer.

My standard casein aggregation substrate is a 1.5% casein solution containing 0.001M $CaCl_2$ adjusted to pH 6.0. This is made by suspending the casein in water, adding sodium hydroxide to raise the pH to 9, heating the suspension to 50 C. to aid in the solution of the casein, adding the stock calcium chloride solution, and then adjusting the pH to 6.0 with a 2M acetate buffer adjusted to 4.7.

For the assay four half dilutions of the sample are made and one ml of each is placed in a test tube. Four ml of the substrate are added to each tube and the tubes are then placed in a 45 C. water bath for one hour. A similar set of dilutions is prepared but to each tube 0.2 ml of a 0.1M cysteine solutions is added before the substrate.

If the sample contains free xeronine and no prexeronine the "no cysteine" tubes quickly become turbid whereas the "+cysteine" tubes have less aggregation and the specific amount of aggregation decreases rapidly with dilution. If the sample contains proxeronine and no free xeronine, the "+cysteine" tubes generally show much more aggregation.

The optical density of the sample tubes and the check are measured at a convenient wavelength. I use 600 nm to avoid interference with colors in certain samples. After plotting the change in O.D. with concentration a decision is made about the possible components of the mixture. With some samples a straight line can be drawn between the points. With others, because of the inhibiting effect of cysteine on the free xeronine reaction and its activating effect in promoting the liberation of free xeronine from proxeronine, the line drawn between the points on the concentration curve may slope either downwards or upwards. This gives a clue about the reactions which have occurred. The CAU value is then calculated:

CAU/unit=(O.D. of sample−O.D. of check)×10

Blood Platelet Assay

This assay, as described by Heinicke et. al. (Experientia 28, 844, 1972) is rapid, requires only a few drops of platelet rich plasma, and is sensitive. Furthermore the assay has a direct relationship to one of the potential applications of xeronine. The disadvantages are that platelets from different people vary in their susceptibility to aggregation by adenosine diphosphate and that certain salts interfere in the reaction.

In the early stage of my research I used this method exclusively.

Smooth Muscle Contraction

This assay, using the smooth muscle from the stomach of a mouse, is excellent for distinguishing between the action of xeronine and proxeronine. Xeronine gives an immediate response causing the muscle to contract more intensely and increasing the frequency of the contraction. By contrast proxeronine gives exactly the same reactions but the response is delayed about thirty seconds and continues for about 30 seconds after the bathing solution containing the proxeronine solution is replaced with the standard salt solution.

Antiinflammatory Test

All critical samples were checked by a standard antiinflammatory test in which an irritant was injected into the skin of a mouse and then the test substance was administered by i.p. injection. After an appropriate time the mouse was killed and a uniform sized piece of skin removed with a punch made in the area of the injection. This was weighed from control and treated animals.

Disc Electrophoresis Assay

For complex mixtures, such as commercial enzymes, the fastest and the best test, is a standard electrophoretic separation in acrylamide gels in tubes. This is run by the standard Ornstein method at pH 4.5. However, at the completion of the run, the gels must be removed as rapidly from the tubes as possible and placed in the dye-fixative solution. If this is not quickly done, the originally sharp band will quickly diffuse and become blurred and difficult to detect.

Also instead of using Coomassie Blue, the protein stain which most biochemists use today, Amido Black stain should be used instead.

Recovery of Xeronine from Natural Sources

The manipulations which must be used for the recovery or xeronine from natural sources are both complex and critical. Certain materials, such as calcium must be present at a critical concentration. Too much or too little will lead to no formation of zeronine. Also certain materials, such as cysteine, act as necessary agents for one phase of the reaction and act as an inhibitor for another phase of the reaction. The directions which I have listed in this invention are specific in their description of the reactions which occur at the molecular level but general in their application to different raw material sources for xeronine recovery. However, a skilled biochemist will have no difficulty in applying the principles which I have enumerated to his specific problem.

The reaction leading to the liberation of xeronine is deceptively simple:

PX + PXase + accessory factors → X where X = xeronine, PX = proxeronine, the precursor of xeronine and the substrate for the enzyme, and PXase is the enzyme which with the appropriate accessory factors leads to the formation of xeronine. However, each of the factors on the left hand side of the equation is itself involved in a series of reactions which greatly complicate the simple reaction pictured above. Let us consider each of the factors separately.

Proxeronine (PX) is a moderately large, complex molecule containing no carbohydrate moieties as measured by the anthrone test and containing no amino acids. The molecular weight appears to be in the vicinity of 4,000. This molecule contains a free SH group which participates in the formation of mixed and homogeneous disulfide molecules. The disulfide form of PX (with one exception) is not active as a substrate for PXase. Therefore in any raw material source for the extraction of xeronine, a preliminary estimate must be made of the possible status of the proxeronine molecules. If the solution contains large amounts of glutathione, a common constituent of many fresh plant extracts, then no sulfhydryl reducing agents need to added to the solution. However, if the plant extract is old or if it has been exposed to air, then cysteine should be added to the solution. Generally if commercial enzyme preparations, such as bromelain, pancreatin, or bacterial protease, are used as a source for recovering xeronine, the assumption can be made that part or all of the proxeronine will be in the disulfide form and that therefore cysteine or a related reducing agent should be added to the solution to reduce the disulfides.

Different proxeronine disulfides vary in their ease of reduction by cysteine or related reducing agents. The mixed disulfide containing proxeronine and glutathione is readily reduced by cysteine at pH 5–8 at room temperature. By contrast the proxeronine-proxeronine disulfide molecule is both extremely insoluble and is also difficult to reduce. This molecule will not dissolve in hot (90 C.) pH 11 solution nor will it dissolve in 0.05M cysteine solution at pH 11. However, if the latter solution is carefully and slowly warmed, the disulfide molecule will be reduced and will still serve as a substrate for proxeroninase. However, if the pH is higher than 11 of if the heating is prolonged longer than necessary to reduce the molecule, then the molecule is destroyed.

Apparently the SH group of proxeronine is not involved in the reaction between the enzyme and the substrate. However, placing a bulky group on the SH group of proxeronine, as occurs during most disulfide formation, blocks the proper positioning of the substrate and the enzyme and accessory factors. Since the SH group is not directly involved in the enzyme action it should be possible to block the SH group of proxeronine with a small group and thus prevent the formation of disulfides. If the blocking group is small enough, it will not interfere with the reaction of substrate and enzyme. Carrying out this blocking reaction both increases the stability and utility of preparations containing proxeronine and also increases the yield of xeronine during the steps listed below. This is another critical part of the invention.

Many different agents can be used as blocking agents. The examples which I am listing are not to be considered exclusive but merely as illustrative. In the laboratory I generally use a simple mercury salt such as ethyl mercuric chloride. This is convenient to use and is able to keep the solutions saturated with trace amounts of mercury at all stages of the isolation steps. Another useful reagent is sodium sulfide. This has two actions. In the initial stage of the reaction it acts as a reducing agent and aids in hydrolyzing disulfide bonds. However, at a later stage, it forms a mixed disulfide with proxeronine. However, since the added molecule is small, it causes no problem in the reaction of the enzyme with its substrate. At pH values above 5 iron salts form a blocking agent which is inexpensive and safe to use for food and medical applications. However, one best blocking agent is a thiosulfate moiety. This can be formed on the SH group by the action of tetrathionate. (See Heinicke, U.S. Pat. No. 3,539,451).

The discovery of proxeronine and an elucidation of its role in the formation of xeronine is a discovery of major importance. Especially important was the demonstration that proxeronine contained a reactive sulfhydryl group and could readily participate in the formation of mixed disulfide bonds. This discovery explained the confusing observations that at times cysteine was essential for biological activity whereas at other times cysteine actually inhibited biological activity. (Cysteine and other free sulfhydryl compounds interfere in the reaction of xeronine and certain of its natural receptors.) The discovery of many mixed disufides containing proxeronine as one component explains the multiplicity of compounds which had distinctive UV absorption spectra but which all eventually produced the same biological action.

To liberate xeronine from its substrate an active enzyme, which I have named proxeroninase, must be present. However, in most natural sources for the recovery of xeronine, this enzyme does not exist in an active form. Instead it exists as a very basic molecule which has an isoelectric point of about 10.5. (See Heinicke and Gortner Economic Botany 11, 225–234, 1957.) A specific amidase probably hydrolyzes the amid groups of surface asparagine and glutamine groups on the protein to convert the protein from a molecule having a very basic isoelectric point to one having an isoelectric point around pH 5.7. Then in the presence of the proper concentration of free calcium ions the modified protein molecules unite to form dimers or trimers. The demonstration that the basic molecules could form dimers with an isoelectric point of about 5.5 was done by Mr. Araki of Jintan Dolph. This work was done independently of the work of Klein and Houck who merely showed that the protein which they isolated with a dimer or timer.

My discovery that a critical concentration of free calcium ions is necessary for the formation of proxeroninase is critical for the reliable formation of this enzyme. Since most substrates normally contain enough calcium ions to act as inhibitors for the formation of the active enzyme, some method must be used to gradually reduce the concentration of calcium ion. If this is carried out, then sometime during the reduction of the free calcium ion concentration the concentration will be optimal for the formation of the di or trimer molecule.

Since most plant and animal tissues contain a variety of molecules which can chelate calcium ions, the simplest method of adjusting the calcium ion concentration at this stage of our information about the composition of animal and plant tissues is to carry out some manipulation which will reduce the calcium ion concentration gradually. Such methods are, but not limited to, simple dilution, passage of a solution of a tissue extract over a cation exchange resin, dialysis, gel filtration, the slow addition of either a calcium chelating agent or else the slow addition of a calcium precipitating agent such as oxalate or phosphate ions at pH values above 5.5 or sulfate ions at any pH. Some examples of uses of these techniques will be given in the examples.

Possibly one of the functions of certain natural chelating agents which occur in cells, such as citrate ions, uronic acids, heparin, as well as certain large complex carbohydrate polymers which contain carboxyl residues is to provide a local concentration of calcium which is optimal for the formation of PXase.

Based upon my preliminary suggested structure for proxeronine, I do not believe that the xeronine molecule exists preformed in the substrate. Instead I believe that proxeroninase is a mixed function enzyme which synthesizes the alkaloid by forming new covalent bonds and then hydrolyzing others. The formation of new covalent bonds generally requires a source of energy which is normally supplied by ATP or by the NAD-NADH$_2$ system. Thus in addition to having the substrate (PX) and the enzyme (PXase) certain accessory factors are required. This is a problem which still requires additional work. However, I have found that either using fresh tissue extracts or else adding extracts of yeast or other microorganisms to the mixture greatly improves the recovery of the alkaloid. I made this discovery when I found that solutions of pineapple stem extracts which had been made from wet stems gave no recovery of xeronine; however, if the solutions were passed over XAD-2 columns and then left on the columns for several days before they were eluted, the recovery came back to normal. During this extended time on the column bacterial growth occurred and probably supplied the critical factors. I subsequently added either yeast or yeast extract to the juice to supply the necessary accessory factors.

Both the discovery that a critical level of calcium ion concentration is required for the active enzyme (PXase) to be formed from the basic proteins and the discovery that certain accessory factors are necessary to obtain good yields of alkaloid are two additional critical factors which will have application in pharmacology and in physiology. Two additional problems still remain to be solved; (1) the factors leading to the activation of the amidases which convert the basic protein into acidic proteins which in the presence of the proper concentration of calcium and the proper pH dimerize to form the active enzyme and the complete elucidation of the nature of the accessory factors which are necessary for the reaction to occur. Nevertheless the information which I am supplying in this patent is sufficient to enable chemists to reliably produce active preparations of xeronine from a wide range of raw materials.

Once the free xeronine is formed and liberated, it generally is quickly used or destroyed. Thus unless special precautions are taken, no free alkaloid will be obtained in spite of having all conditions necessary for the production of the xeronine. Part of the destruction of the xeronine is enzymatic and part is a simple oxidative destruction of the molecule. The enzymatic destruction can best be limited by adjusting the pH of the solution to a point where the enzyme is inactive. The referred pH is on the acid side, namely pH 3.0 to 4.5. This low pH also appears to lessen the oxidative destruction of xeronine. Another method of eliminating the enzymatic destruction of xeronine is to heat the solution to 65 C. for 15 minutes. This also has the advantage of destroying all of the proteases which—in spite of the present pharmacological practices—are undesirable for most pharmacological applications. Still another method of stabilizing the liberated xeronine is the formation of salts. Both organic and inorganic salts are effective. With pineapple stem extracts one of the simplest salts to recover is one formed between xeronine and silicic acid. The pineapple stem juice is very high in soluble silicates. In the presence of cations, including xeronine, the silicates can be precipitated by raising the pH above 6. Thus it is possible to both isolate xeronine as a silicate salt complex and also to stabilize the xeronine. Another natural salt complex which forms readily and can be isolated by precipitation with acetone is the ferulic acid rich, complex carbohydrate polymer which is found in pineapple stem juice. (Levand and Heinicke, Phytochemistry 7, 1659–1662,) 1968).

Isolation of Xeronine

The critical step in the isolation of xeronine is the liberation of xeronine from the natural precursors. This subject was covered in the previous section. Once the alkaloid has been liberated, then any of the classical techniques of alkaloid chemistry are usable for isolation and purification. These include, but are not limited to, partition between organic and aqueous phases by changing the pH, adsorption on either strong or weak cation exchange resins, adsorption of adsorbents such as carbon or proteins by raising the pH above 6.5 to lower the solubility of the alkaloid in water, by distillation, or by precipitating the alkaloid as an insoluble salt. Some examples of these techniques, but not limited to them, will be given in the section on examples.

There are many feasible source materials suitable for the isolation of xeronine and the present invention should not be construed as limited to any particular source materials.

Xeronine may be isolated from a wide variety of plant sources. Particularly rich sources are those plants which have a growth pattern in which rapid growth periods alternate with long periods of quiescence. Some of these are the Bromeliaceae, the Ficus family, the Euphorbiaceae, the Caricaceae, some compositaceae, and many desert plants. Particularly promising as raw materials are those plant which are already planted in groves or plantations, such as rubber trees, pineapple, and agave and hennequin.

Xeronine may also be isolated from microbial sources. Here the critical factor is not so much the species of microorganism which is selected as is the growth cycle in which the organism is harvested.

Animals are also a potential source of xeronine. The richest sources are extracts of the stomach lining and pancreatic secretion.

Instead of the original raw material, extracts of these tissues can also be used as a raw material for isolating xeronine. Some examples of such extracts are "bromelain", papain, rennet, pancreatic amylase, fungal protease and salmon milt.

Physiological Action of Xeronine

Xeronine's physiological action appears to be as a modifier of the rigidity of specific proteins. Thus it can have a wide range of effects depending upon the function of the protein; it can convert certain specific inactive proteins into active enzymes. For example the action of xeronine with kappa casein converts this protein into an enzyme which can liberate by autodigestion a specific polypeptide. This action explains how xeronine coagulates casein. It may also activate the body collagenase, on action which could explain the unique ability of certain preparations made from the pineapple plant to debride burn eschars by a well recognized collagenase action. It is the factor which converts certain inactive plant and bacterial amylases into active amylase.

If the protein receptor occurs on a cell membrane, then the reaction of xeronine with the receptor may affect the transfer of materials into the cell. The cell membrane receptors very likely require both a specific hormone as well as xeronine before a specific reaction occurs. This dual requirement could explain why "bromelain" may simulate the action of certain hormones, such as the prostaglandins, insulin, adrenaline, the milk secreting hormone, and many other diverse types of hormones.

One of the outstanding properties of xeronine is its great physiological activity even at extremely high dilutions. Based on its action in activating the proenzymes of seed fragments of barley, I estimate that it still shows biological activity at a dilution of $10^{-10}$ g of xeronine per gram of substrate. This makes biological assay of xeronine sensitive and easy to measure but makes chemical work with this material very difficult because of the problems in isolating sufficient quantities of the material for conventional chemical analysis.

APPLICATIONS OF XERONINE

Pharmacological Application

Every pharmacological action of such "enzymes" as bromelain, bacterial proteases, and pancreatin may be ascribed, I believe, solely to a potential source of xeronine which these enzymes may contain.

This belief is based on the demonstration that samples of xeronine prepared by distillation, and which therefore could not possibly contain peptides, amino acids or steroids, acted as excellent antiinflammatory agents when injected into mice, inhibited the in vitro aggregation of blood platelets by adenosine diphosphate, caused the debridement of burn eschars on mice, stimulated the partial breakdown of wheat grits, and caused the aggregation of casein. All of these are reactions formerly imputed to such proteases as "bromelain" pancreatin, and *Serratia marcescens* protein. Therefore standardized preparations of xeronine should be more effective for all of the present medical, food, and industrial applications of bromelain and the other enzymes since these are improperly standardized and therefore unreliable in performance.

However, there are several important new applications for xeronine. My demonstration that the active ingredient in many of the pharmacologically active enzymes and in many of the effective folklore drugs is an alkaloid, namely xeronine, and that this alkaloid can be recovered from animal and bacterial sources, indicates that this alkaloid is a critical normal metabolic coregulator. Therefore one would predict that xeronine would be an effective antidote against alkaloid poisoning and addiction. In the examples I have shown that a relatively pure sample of xeronine was an almost perfect antidote for tetrodotoxin, the most toxic alkaloid known. This confirmation of the theory led me to suggest that xeronine should be a specific cure for nicotine and hard drug addiction. We have tested crude preparation of xeronine on confirmed smokers and have had a 90% cure rate with no tension involved during the withdrawal period. With hard core drug addicts, xeronine should provide a true cure with no withdrawal symptoms. Preliminary tests with crude preparations of xeronine have shown complete cures of hard core drug addicts with no withdrawal symptoms and with no dependency on a substitute alkaloid.

Another critical potential application for xeronine is for the alleviation of the symptoms of one type of senility. This observation was originally made by Gus Martin with a sample of enzyme which I had prepared in the early phases of my research. This particular sample was made into pills and given to a woman who had been senile, uncomprehending, immobile, and incontinent for three months. Two hours after taking the pill she sat up in bed, asked why she was there and began asking for her family. As long as she was taking the pills, she was a normal, functioning person again and took a very active part in the hospital program. When the supply of this batch of pills ran out, an "improved" batch of bromelain pills was substituted. Three days later she lapsed into her former senile state. Until my recent work on xeronine, I had been unable to repeat or to explain why this one batch of bromelain behaved so spectacularly.

Another important new application for xeronine will be as a general stimulant or tonic. In the tetrodotoxin experiment mentioned above, the control mice which had been injected with xeronine only, became very alert and explored their cage for about a half an hour before they also burrowed into the shavings as the saline injected mice had done immediately after being injected. Based on this behaviour in mice I drank a solution of xeronine containing about 50 times as much xeronine as the mice had received. The pleasant, stimulating, alert feeling lasted until about three o'clock in the morning. This is a response which is similar to that reported by Russian scientists for extracts of high quality ginseng or Eleuthrococcus.

In summary as far as the medical applications of xeronine are concerned my discovery that xeronine can counteract the effects of foreign alkaloids will suggest many new and important applications in medicine. Also another discovery which will have important medical applications is my finding that xeronine acts as the coregulator for many hormone actions. This suggests that the body has a two component system for regulating and integrating the metabolism of different tissues; hormones, which are secreted into the blood stream and contact all tissues and xeronine, which is produced locally by the tissue and determines whether or not that tissue will respond to the presence of the hormone in the blood. Both factors must be present for a response to occur. This theory suggests that many problems, such as diabetes, may be caused either by a lack of the hormone, insulin, or by the lack of xeronine in the cell membrane at the local level. Both must be present for the cell to properly absorb and metabolize glucose.

In plants xeronine has another function in addition to a possible role as a coregulator with secreted hormones. In the pineapple plant xeronine converts certain precursors of catabolic enzymes into the active form. Thus the liberation of xeronine, through its action in forming active hydrolases, converts stored food material, such as starch, proteins, and organic phosphorus compounds into soluble sugars, amino acids and phosphorus. These can be used either to produce new growth or to mobilize food for storage in seeds or tubers.

This action has great utility in modifying the properties of such food seed materials as peas, corn, lima beans, beans, wheat, rice etc. into products in which the starch is partially broken down into sugar, thus producing a sweeter and more tender product. Such an action also has great value in hastening the germination of seeds by stimulating the conversion of the stored food products into simple usable molecules.

Another food application of great utility is my discovery that xeronine can stimulate the action of commercial rennet. This discovery now provides the food technologist with a method of forming a milk curd which can be used as a basis for making cheeses. Since the action of xeronine is limited solely to the clot forming action and since there is no secondary proteolytic effects to consider, the scientist now has complete control over the cheese manufacturing process.

EXAMPLES

A. Isolation of Xeronine by Various Techniques from Various Raw Materials

In the examples given below the assumption is made that either conditions have been arranged so that free xeronine has been liberated from the precursors or else that the technique used will allow free xeronine to be released during the isolation process.

A1 By Adsorption and Elution from XAD-2

Ex. 1 From Commercial Grade Bromelain

An XAD-2 column was thoroughly cleaned and then rinsed with dilute HCl followed by water to leave a slightly acidic reaction on the column. Twenty grams of commercial grade bromelain was suspended in one liter of water and then mixed with one liter of acetone. The solution was centrifuged, the precipitate discarded and the supernatant solution slowly run through the column. The percolate, which consisted of a mixture of proteins, peptides, sugars, salts and simple organic acids which were soluble in 50% acetone was discarded. After the column was thoroughly washed with a 50% acetone solution, the material adsorbed on the column was eluted with one liter of a 50% acetone solution containing sufficient ammonium hydroxide solution to raise the pH to 10.5.

The eluate, which was straw colored and had a pH of 9, was adjusted to pH 4.5 and the acetone stripped off under a vacuum. The insolubles which formed during this stripping step consisted of denatured protein and proxerine residue and were discarded. The clear supernatant solution was then run over a freshly cleaned XAD-2 column, the percolate collected, and the solution concentrated to 15 ml. At this concentration ammonium salts crystallized out. These were discarded. The clear supernatant solution was then freeze dried.

Because of the high salt concentration, this took several days.

Weight recovered (mostly ammonium salts) 12.5 g.

Xeronine units per mg=1.8 CAU or 22,500 CAU total/20 g.

The salt prepared from this and similar runs was further purified by the techniques described in Section B of the Examples.

Ex. 2. From Commercial Rennet Powder

The excellent recovery of xeronine by the emulsion technique (Ex. 6) indicated that additional tests were warranted.

Fifteen grams of commercial rennet powder (Nakari) were suspended in one liter to water. Because of the strong odor, the pH was dropped to 3.5 and the simple organic acids extracted with chloroform. An equal volume of water was added to the aqueous portion, the mixture centrifuged, and the precipitate discarded.

The acetone supernatant solution was then run over a freshly washed XAD-2 column, the column rinsed with 50% acetone and the adsorbed material then eluted with one liter of 50% acetone which had been adjusted to pH 10.8 with ammonium hydroxide solution.

The pH of the eluate was then adjusted to pH 5.0 and the acetone and the water removed under a high vacuum. To the dry salts 10 ml of a pH 10 1 M borate solution was added and the solution distilled under a high vacuum.

The distillate had a strong nicotine-like odor. The pH was adjusted to pH 7.0 and the solution evaluated as an antiinflammatory agent for the prevention of edema in mice. It gave better protection against edema than the standard test solution of bromelain which was used in these tests.

A2. By Passage Over Combinations of Ion Exchange Resins

Ex. 3. The Acetone Still Aqueous Residues from a Commercial Bromelain Production Plant Five gallons of the acetone still residues were passed in series over a strong cation resin (c-20) in the hydrogen form, over a macroreticular non-ionic resin, and over a weak cation resin (IRC-84) in the ammonium salt form. The final percolate solution was discarded.

The weak cation column was eluted with 5% acetic acid and those eluates saved which had a pH between 7 and 4.5. The solution was concentrated on a thin film evaporator under a high vacuum. As the ammonium acetate salts began to crystallize, they were removed and discarded. The thick syrupy residue was then freeze dried. During the freeze drying step additional ammonium acetate distilled from the freezing flask.

| Total weight of ammonia acetate + xeronine | 77.45 g |
|---|---|
| Average CAU/mg | 5 |
| Total recovery from one gallon | 77,450 CAU |

Of about 15 runs by this method, this recovery was considerably above the average. During this isolation the adsorbed material remained on the column for three days before it was eluted. This long holding step, under conditions which were favorable for the release of free xeronine from the precursors, is probably responsible for the excellent recovery of xeronine.

A UV spectrum of this product showed a single sharp peak at 253 nm and a small peak at 215. This particular batch of xeronine was used in many of the tests of possible applications of xeronine.

Ex. 4. Recovery of Xeronine from Bromelain by Combined Ion Exchange Resins

To a solution of 5 grams of bromelain adjusted to pH 3.8, an equal volume of acetone was added and the precipitate was removed and discarded. After the acetone was removed from the supernatant solution under a vacuum, the aqueous residue was run over a strong cation resin in the acid form (C-20) and then over a weak anion resin (IRA-84) and finally over a weak cation resin (IRC-50) in the ammonium salt form.

The weak cation resin was eluted with 5% acetic acid, the solution concentrated, part of the ammonium acetate removed as crystals and the residue freeze dried. During the freeze drying operation, additional ammonium acetate was removed as a volatile salt.

| Weight of recovered salt/5 g bromelain | 2.8 g |
|---|---|
| CAU/mg | 4.3 |
| Total CAU recovered /g enzyme | 2408 |

Ex. 5. From Pancreatic Amylase

Seventy five grams of hog pancreatic amylase were dispersed in 850 ml of water containing 2 g of ascorbic acid. The pH was adjusted to 4.5 and the insolubles removed. To the supernatant solution an equal volume of acetone was added, the precipitate removed, and the acetone evaporated in a thin film evaporator. During the evaporation of the acetone a precipitate formed. This was removed. (Later studies indicated that this precipitate should have been saved as a source of proxeronine.) The clear solution was first run over a strong cation column (C-20) in the acid form, then over a non-ionic macroreticular resin (XAD-2) and finally over a weak cation in the ammonium salt form (IRC-84).

The IRC-84 column was rinsed first with water and then with 100% acetone. (Later studies showed that some xeronine could have been removed by this last step). The column was then eluted with 5% acetic acid. Xeronine activity started to appear in the eluate when the pH of the column had dropped to 6. Elution was continued until all of the column was in the hydrogen form.

| First portion of IRC-84 eluate after pH 6.0 | 30 g salt | 0.22 CAU/mg |
|---|---|---|
| Next portion | 32 g salt | 0.09 CAU/mg |
| Last portion | 28 g salt | 0.0 CAU/mg |

The recovery of CAU was 126.4 CAU/g of amylase. Whereas this is not as high as from other sources, this is acceptable considering that potential activity was lost in two fractions, the precipitate which appeared when the acetone was removed from the first supernatant solution and the acetone wash of the IRC-84 column.

A.3 By the Emulsion Technique

Ex. 6. From Commercial Rennet Powder

Four grams of commercial rennet powder (Nakarai) were dispersed in 150 ml of water and the pH adjusted to 5.7. After an hour the pH was raised to 10 and the solution was vigorously shaken with and extracted with two 50 ml portions of chloroform. After centrifuging the similar fractions were combined. The tight emulsion layer was broken by adding five volumes of methanol and then centrifuging the suspension to remove the precipitated proteins. The solvents were removed from all samples and the solutions assayed.

| | |
|---|---|
| Aqueous phase | 0 |
| Emulsion precipitate | 0 |
| Emulsion supernatant solution | 83,480 |
| Clear chloroform layer | trace |

Ex. 7. From Commercial Bromelain

Five hundred ml of a 2% bromelain solution were mixed with sufficient cysteine to give a 0.01M solution and the pH then adjusted to 8.5. Twice the solution was vigorously shaken with 50 ml of chloroform in a separatory funnel to promote the formation of a tight emulsion. The solutions were centrifuged and the similar fractions combined. The clear chloroform layer was extracted twice with 50 ml of pH 3 buffer and the aqueous phase used for assay. The emulsion layer was mixed with four volumes of acetone and the mixture centrifuged to remove the precipitated colloids. The solvent was removed from the supernatant solution and the aqueous residue assayed.

| | Not Boiled | Boiled | |
|---|---|---|---|
| Aqueous layer | (Protease) | 0.2 CAU/ml | 100 total |
| Extract of chloroform layer | 14 CAU total | 0.3 CAU/ml | 12 total |
| Emulsion layer | 160 CAU total | 12 CAU/ml | 150 total |

The recovery of xeronine in this experiment was low compared to the recovery on XAD-2 columns or on ion exchange resin columns. The difference could be partly a time factor. In the emulsion technique used in this example, the run was completed in about ½ hour. By contrast in any of the column techniques, a run generally takes from 5 to 48 hours. This longer time permits more opportunity for the enzymatic formation of xeronine. Also in the short run used in this emulsion example, the sample was at an unfavorable pH for enzymatic action most of the time.

The recovery of activity in this example should be compared with the excellent recovery from rennet powder (Ex. 6) or from ficin (Ex. 8) using a similar technique but including a holding step at pH 5 of one hour to promote the liberation of xeronine.

Ex. 8 Recovery of Xeronine from Ficin by the Emulsion Technique

Ten grams of commercial grade ficin was suspended in 200 ml of water and the pH adjusted from 5.0 to 3.5. The organic acids were then extracted from this solution with chloroform. The pH of the solution was then raised to 5 and the solution held for a half an hour for the possible liberation of free xeronine from the precursors.

The pH of the solution was then raised to 9.7 and the solution shaken vigorously with 50 ml of chloroform to form an emulsion. The mixture was centrifuged to break the weak emulsions and to give a three phase solution, a very tight, stable emulsion layer, and a clear chloroform layer. The chloroform layer was extracted with pH 3 aqueous buffer to extract any bases from the chloroform layer. The emulsion layer was broken and the colloids precipitated by adding four volumes of methanol to the solution and centrifuging. Both the aqueous supernatant solutions and the two fractions from the emulsion layer were boiled before assaying for CAU activity.

| | Assayed for CAU | | | |
|---|---|---|---|---|
| | No cysteine | | Added cysteine | |
| Aqueous supernatant solution | 2/ml | 400 total | 4/ml | 800 total |
| Emulsion layer; precipitate | 0 | 0 | 0 | 0 |
| Emulsion layer; supernatant | 29.1 | 14,560" | 52.5 | 26,260" |

The recovery of 2626 CAU/g of enzyme compares favorably with the recovery from bromelain by the better techniques.

Note that in this example the recovery of xeronine was much higher than in Example 8 with bromelain. In that example no opportunity was allowed for the enzymatic liberation of xeronine before the extraction technique.

A6. By Gel Filtration

Ex. 9. From Commercial Bromelain

This example is given not as a potential commercial method for producing xeronine but as an illustration of the liberation of xeronine from colloids in bromelain. The experiment described in this example was run twenty times at different pH adjustments of the gel filtration column and of the enzyme solution.

To summarize the results, I found the best recovery of xeronine when the column and the enzyme solutions were adjusted to pH values between 4–5. Below pH 3.5 the recovery of xeronine dropped to negligibly low values. Between pH 6 to about 8 the recovery was 0. From pH 8.5 to 10.5 the recovery of xeronine was present but only about a third as large as at pH 4–5. I have illustrated below one such a test.

After equilibrating a G-15 Sephadex column with the desired buffer, I added 5 ml of a 1% solution of bromelain to the column and developed the column with buffer. All tubes were assayed for protease activity, for CAU, for pH and for UV spectra.

With the column and the collection volume which I used, the protease appeared in tube 8, peaked at tube 9, and passed out of the column by tube 11. The first material to emerge from the column was a large, complex aggregate. This contained large amounts of an acidic carbohydrate polymer, small amounts of a non-proteolytic enzyme, acid phosphatase, peroxidase, and lipophyllic materials. This aggregate consistently appeared in tube 6, peaked at tube 7, and trailed into tube 8. Xeronine was liberated from this colloidal complex and generally appeared in tube 7. Some of the liberation apparently occurred as the colloids were migrating down the column. This caused a tailing of the xeronine activity across all of the tubes. Much of the xeronine was liberated in the collection tubes since an immediate assay of the activity was frequently less than one tenth the value found after six hours.

When the tubes containing xeronine from different runs, that is tubes 6–7, were combined, concentrated, and then rerun on the column, the xeronine activity now appeared in tubes 15–18. These experiments conclusively demonstrate that xeronine is liberated from materials which are present in bromelain.

B. PURIFICATION

B1. By Gel Filtration

Ex. 10. Of salts from an XAD-2 Isolation Procedure 500 mg of the preparation from example #1 were dissolved in three ml of water and placed on a Sephadex G-15 gel filtration and developed with water. Ten ml fractions were collected. All fractions were checked for pH, for CAU and for the UV spectrum. All of the activity appeared in essentially one tube, #17. This gave a spectrum which indicated that the fractions were still a mixture of peptides and xeronine. The UV absorption curve indicated that part of the absorption was caused by the 253 nm form of xeronine.

B3. By Distillation

Ex. 11. of Salts from an XAD-2 Isolation Procedure of Bromelain

Five grams of the salt from Example 1 were dissolved in 50 ml of water, the pH raised to 9.5 and the solution distilled under a high vacuum with a dry-ice acetone cooled receiving flask. A mixture of ammonia vapors, water and xeronine distilled over and froze in the flask. When the frozen mass was melted about five micrograms of xeronine crystals floated on the surface of the basic solution.

Xeronine crystals prepared by this method were used for mass spectral analysis, for biochemical assays, for pharmacological assays, and for physiological studies.

Although xeronine prepared by this method is of excellent purity, the recovery is low, about 1 to 2%. Apparently at the high pH used for the distillation, a large portion of the xeronine is destroyed. What distilled over had the typical nicotine-like odor which is characteristic of good samples of xeronine. This odor is so distinctive, that xeronine can be recognized on the basis of the odor alone.

Ex. 12. Protecting the SH Group of Proxeronine with Iron and Ascorbate

This example illustrates the use of ferrous sulfate and ascorbate combinations to lessen the potential oxidation of the SH group of proxeronine to form disulfides which are inactive.

Four 100 ml solutions of 1% bromelain were mixed with various combinations of iron and ascorbate at pH 8. After one hour at room temperature 150 ml of acetone was added to each beaker and the precipitated colloids were removed. The pH of the supernatant solution was dropped to 5 and the acetone removed on a thin film evaporator. All solutions were boiled to destroy any residual protease activity, the pH raised to 10 and each solution shaken vigorously with 50 ml of chloroform. Assays for casein aggregating activity were run on both the aqueous layer and on an acid extract of the chloroform layer with the following results.

| Treatment per 100 ml | | CAU Activity in | |
|---|---|---|---|
| ml 20% $FESO_4$ | g ascorbate | Aqueous layer | $CHCL_3$ layer |
| 0 | 0 | 57 | 30 |
| 0 | 1 | 300 | 56 |
| 4 | 0 | 320 | 53 |
| 4 | 1 | 280 | 56 |

Experiment 13. Recovery of Xeronine from Poor Quality Acetone Still Residue

This particular batch of acetone still residue came from a batch of wet stumps which had been processed for bromelain. A UV spectrum analysis of the solution showed a total lack of any material absorbing at 275 nm. This peak is a UV indicator of the quality of the raw material. When this batch of solution was processed by exactly the same technique used in Example 3 on the same columns, the recovery of xeronine from any column was negligible.

This poor batch of juice was concentrated to ¼ volume and the solution was set aside in the refrigerator for several weeks. During this time a mold grew on the surface of the solution. This was removed and the juice processed by passing one liter of the concentrated solution over an XAD-2 column which had been rinsed with dilute acid. This treatment removed most of the colored material.

In contrast to the behaviour of solutions of bromelain-acetone supernatants, as in Example 1, in this run all of the CAU activity appeared in the initial percolate solution from the column. None of the eluate solutions contained any activity. This indicates that the reactions liberating free xeronine had occurred in this poor batch of acetone supernatant solution during the several week holding period. Presumably accessory factors supplied by mold as well as a gradual precipitation of calcium salts which occurred during this long holding period, allowed the basic proteins to form active proxeroninase. This together with the accessory factors led to the formation of free xeronine.

Before the several week incubation period and the addition of accessory factors through the growth of molds, the total recovery was about 5,000 CAU/gallon. After the treatment described above the recovery was 64,000 CAU/gallon which compares favorably with the best of the recoveries from this source.

This is a critical discovery.

C. APPLICATIONS

Ex. 14. Lessening of Blood Clot Formation on Intravenously Inserted Catheters

The Amplatz method (Durst, S; Leslie, J; Moore, R; and Amplatz, K. Radiology 1974; 599–600) was used to form and quantitate clot formation.

Before a 30 cm length of catheter was inserted into the femoral artery of 25–30 kg dogs, a 7 CAU/ml solution of xeronine in saline was pumped into the forepaw vein at the rate of 50 ml per hour. The injection was continued as long as the catheter was kept in the vein. After an hour the catheter was removed, and the adhering clot weighed.

Immediately after removing the catheter and after discontinuing the injection of xeronine into the animal, a fresh catheter was placed in the artery and left in the animal for an hour. It too was then removed and the adhering clot, blotted and weighed.

| | |
|---|---|
| Weight of clot before injection | 309 mg |
| Weight of clot during xeronine injection | 158 mg |
| Weight of clot one hour after discontinuing injection | 299 mg |

In another experiment enteric coated bromelain granules were fed to the animal one hour before the catheters were inserted. The catheters were then placed in the femoral artery every hour, removed, and the weight of the adhering clot weighed.

| Weight of Adhering Clot at Different Intervals After an Oral Dose of Bromelain | | | | |
|---|---|---|---|---|
| One Hour | Two Hours | Three Hours | Four Hours | Five Hours |
| 380 mg | 142 mg | 150 mg | 205 mg | 287 mg |

The advantage of the xeronine injection technique over giving a potential source of xeronine orally is that the effect on the rate of blood clot formation is immediate and continues only as long as the injection is continued. This technique would have great utility in medicine over the standard heparin technique.

Ex. 15. Effect of Xeronine on in vivo Meat Tenderization

One ml of physiological saline containing either 0, 4 or 10 CAU of xeronine or a highly purified sample of bromelain at the rate of 20 mg/kg was injected into the wing veins of four 18 month old cocks. None of the samples caused any visible distress to the chickens. Five minutes after the injection the chicken were killed and dressed on a commercial processing line.

The chickens were cooked in a restaurant style oven by a professional cook and coded samples of the breast meat presented to four judges. No detectable differences were noted in the flavor of the chickens. There was marked difference in the tenderness.

| Ranking of the Tenderness of Meat on a 1-5 Scale 1 = very tough, 5 = very tender | |
|---|---|
| 0 CAU/ chicken | 2,3,1,2 |
| 4 CAU/ chicken | 3,2,2,3 |
| 10 CAU/ chicken | 3,5,5,4 |
| Purified bromelain | 1,1,2,1 |

The bromelain sample had been purified by ammonium sulfate precipitation, dialysis, and gel filtration. It contained 3200GDU/g in contrast to the standard 1200GDU/g for standard bromelain. What is surprising is that this sample caused no visible distress to the chicken. Normally commercial grade bromelain has an L.D.-50 of 15 mg/kg. Also this excellent protease sample actually increased the toughness of the meat.

The xeronine sample contained no trace of protein or polypeptides. Therefore the tenderizing action must be solely attributable to the action of xeronine in activating the cathepsin hydrolases in the chicken muscle.

Ex. 16. Hydrolysis of Seed Starch

Xeronine hydrolyses seed starch by activating the proamylases contained in the seed.

To 10 g of ground barley seed either 1 ml of buffer or 1 ml of buffer containing 2 CAU of xeronine (prepared by the method shown in Ex. 3) were added and the mixture held at 40 C. for one hour. One hundred ml of water were then added to each sample and the suspensions placed in a boiling water bath for exactly one minute. The mixture was then centrifuged and the supernatant solution decanted.

| | ml supernatant solution | Viscosity of solution |
|---|---|---|
| Control | 51 | similar to water |
| Xeronine treated | 43 | so viscous that it was difficult to pour |

This example illustrates the powerful action of xeronine in converting one form of stored food, the starch, to soluble forms through the activation of endogenous enzymes.

Ex. 17. Action on Casein

This example illustrates the ability of xeronine to liberate a peptide from casein similar to the action of the so-called "milk clotting" enzymes. Since this sample of xeronine had been boiled, there is no possibility that the action could have come from contaminating proteases. The xeronine sample was prepared as in Example 3.

To 100 ml of a 1% Hammarsten casein solution were added 25 CAU of xeronine. Five ml samples were removed from the solution (at room temperature) at the times indicated, and mixed with 5 ml a precipitant. The precipitant contained 6% trichloracetic acid, sufficient acetate to give a molarity of 0.2 M and a pH of 4.8. The precipitate was removed by filtration through a fine grade filter paper. To 2 ml of the filtrate were added 2 ml of a 4% NaOH solution and 1 ml of biuret reagent. The biuret color was read at 545 nm against a reagent blank.

| | Time of Sampling | | | | | |
|---|---|---|---|---|---|---|
| | 0 | 4 | 90 | 150 | 170 | 210 |
| Net increase in biuret color | 0 | 5 | 20 | 60 | 40 | 40 |

That this reaction reaches a plateau indicates a reaction limited by the availability of additional substrate. This type of reaction is very different from that found with a standard protease, such as bromelain, in which the liberation of peptides continues for many hours.

Ex. 18. Action on Milk

A sample of xeronine prepared by distillation (Example 11) was added to commercial skim milk and the mixture held at 45 C. A typical clot formed which showed syneresis within one hour.

Since this ample of xeronine could not possibly contain protease contaminants because of the method of preparation, and since this sample simulates the action of commercial rennet solutions on casein, this example illustrates the utility of xeronine for cheese manufacture.

Ex. 19 Effect of Xeronine on Bleeding Time

This action can only be detected in animals or people who have been stressed. In this experiment adrenaline was used as a stressing agent.

| The Effects of Xeronine on the Bleeding Time of Mice Which Had Been Injected with Adrenaline One Hour Previously | | | | | | | |
|---|---|---|---|---|---|---|---|
| | Treatment | | | | | | |
| | | Time | Bleeding | Significant Differences | | | |
| Code | Time 0 | 60 Min. | Time | AX | BX | AB | BB |
| AX | Adrenaline | Xeronine | 202.7 | — | — | — | — |
| BX | Buffer | Xeronine | 150.7 | — | — | — | — |
| AB | Adrenaline | Buffer | 129.1 | ** | no | — | — |
| BB | Buffer | Buffer | 122.6 | ** | no | no | — |

The mice were bled five minutes after the xeronine injection. The volumes used for i.p. injection were all 0.25 ml. The results were analyzed statistically with the odds shown. The * denotes differences significant at the 5% level; the ** denotes differences significant at the 1% level. The amount of adrenaline used was 0.1 mg per kg.

Ex. 20. Effect of Xeronine on Inflammation

The rats were fasted overnight and then given 0.7 ml of either a solution of xeronine in 0.005M cysteine or else 0.7 ml of physiological saline containing 0.005M. cysteine. One hour later each rat was injected subcutaneously with 0.05ml of an anti-rat serum. Two hours later the rats were killed and the extent of the edema was measured by punching out a piece of skin at the site of injection and weighing the punched skin.

The results are statistically significant.

The Effect of Orally-Admininstered Xeronine on Serum-Induced Inflammation as Measured by the Punch Method

| | Control | Treated | |
|---|---|---|---|
| | 117 | 86.1 | |
| | 133 | 115 | |
| | 117 | 110 | |
| | 127 | 77.7 | |
| | | | "t" test |
| | 133 | 115 | |
| | | | $t_o = 2.86$ |
| Sum | 627.3 | 503.8 | |
| | | | $t_{.05} = 2.31$ |
| Average | 125.5 | 100.8 | |

MISCELLANEOUS

Example 21 Analysis of Complex Samples for Free Xeronine

Up to about 1964 the electrophoretic patterns run at pH 4.5 of all bromelain samples prepared by Dole contained a thin, fast moving band which stained blue with Amido Black stain. Since about 1966 none of the Dole samples nor none of the Taiwan samples contained this fast moving band. This fast moving band represents free xeronine.

The sample was prepared by the method used in Example 3. When applied to a disc electrophoresis column and run at pH 4.5 a 5 mg/ml concentration gave no visible bands. However, at 50 mg/ml a thin fast moving band, which was easily visible without staining, moved down the column. During the interval between removing the sample gels from the tubes and staining them with Coomassie Blue, about 20 minutes, the band spread appreciably, indicating a small molecule. The dye solution in the tube contained an appreciable amount of precipitate indicating that a fast diffusing molecule moved out of the gel and reacted with the stain faster than the stain moved into the gel.

This band, which moved twice as fast as the fastest protein band in bromelain (which has an isoelectric point of about 9.5), was cut out and tested for both its casein aggregating properties and also for its ability to inhibit the aggregation of blood platelets which had been exposed to different concentrations of adenosin diphosphate. Its positive action in both tests indicates that the band contained xeronine.

Of the two dyes, Coomassie Blue and Naphthol Black, normally used as protein stains in disc electrophoresis, the latter, with a molecular weight of 616 is superior to the former, M.W. 854. With naphthol black the spread of the band and the loss of material by diffusion into the tube is less since the diffusion rates of the dye and xeronine are more similar.

Although the invention has been described with reference to specific embodiments, the exact nature and scope of the invention is defined in the following claims.

I claim:

1. A new composition of matter called Xeronine formed by the process comprising:
   obtaining source materials selected from the group consisting of plant bacteria and animal alkaloid producing lipophilic extracts, combining lysozymes with the extracts to produce a mixture, controlling the concentration level of free calcium ions in the mixture to produce an optimum concentration level which activates the lysozymes, and controlling the pH of the mixture of the range of about 3.5–5.0 to react to the extracts with the activitated lysozymes to produce the active substance xeronine, having a molecular weight between 413 and 518, having four forms, three of which convert to a fourth form irreversibly by manipulation of temperature and pH, adapted to be adhered to specific proteins as a modifier of rigidity of a consequential wide range of effects.

2. The composition of claim 1 having a form generated by heating at a temperature of about 60 C. and a pH of about 1.5–2.0 for 24–48 hours.

3. The composition of claim 1 having a form generated by heating at a temperature of about 80–90 C. and a pH of about 9.5 for 10 minutes.

4. The composition of claim 2 wherein the form is altered by further warming and increasing the pH to 12.

5. The composition of claim 3 wherein the form is altered by further warming and increasing the pH to 12.

* * * * *